(12) United States Patent
Rothbard et al.

(10) Patent No.: US 7,820,626 B2
(45) Date of Patent: Oct. 26, 2010

(54) COMPOSITIONS AND METHODS FOR TREATING DISEASES

(75) Inventors: Jonathan B. Rothbard, Woodside, CA (US); Paul L. McGrane, Mountain View, CA (US); Edgar G. Engleman, Atherton, CA (US); C. Garrison Fathman, Portola Valley, CA (US); Erik Kreider, Boulder, CO (US)

(73) Assignee: Lumen Therapeutics, LLC, Menlo Park, CA (US)

( * ) Notice: Subject to any disclaimer, the term of this patent is extended or adjusted under 35 U.S.C. 154(b) by 0 days.

(21) Appl. No.: 12/258,265

(22) Filed: Oct. 24, 2008

(65) Prior Publication Data

US 2009/0053283 A1 Feb. 26, 2009

Related U.S. Application Data

(63) Continuation of application No. 11/736,689, filed on Apr. 18, 2007, now Pat. No. 7,557,087, which is a continuation of application No. 11/070,528, filed on Mar. 1, 2005, now abandoned.

(60) Provisional application No. 60/549,321, filed on Mar. 1, 2004.

(51) Int. Cl.
    *A61K 38/03* (2006.01)
    *C12P 13/10* (2006.01)

(52) U.S. Cl. .................. 514/21.7; 514/1.1; 435/114; 530/328

(58) Field of Classification Search .................. None
See application file for complete search history.

(56) References Cited

U.S. PATENT DOCUMENTS

| | | | |
|---|---|---|---|
| 5,364,884 A * | 11/1994 | Varma et al. ................. | 514/551 |
| 5,428,070 A | 6/1995 | Cooke et al. | |
| 5,504,117 A | 4/1996 | Gorfine | |
| 5,873,359 A | 2/1999 | Zapol et al. | |
| 5,919,761 A | 7/1999 | Wakefield et al. | |
| 6,156,975 A | 12/2000 | Roos | |
| 6,358,536 B1 | 3/2002 | Thomas | |
| 6,495,663 B1 | 12/2002 | Rothbard et al. | |
| 6,593,292 B1 | 7/2003 | Rothbard et al. | |
| 2002/0086829 A1* | 7/2002 | Gefter ...................... | 514/12 |
| 2002/0198136 A1* | 12/2002 | Mak et al. ..................... | 514/1 |

OTHER PUBLICATIONS

[Retreived from]: http://healthlibrary.epnet.com/GetContent.aspx?token=0a1af489-5b4c-4f2d-978e-3930be13b1f6 &chunkiid=199430, 4 pages, 2010 [Retreived on Jan. 22, 2010].*
[Retreived from]: http://www.medicineonline.com/articles/P/2/Pudendal-Neuralgia/Vulvodynia.html, 4 pages, 2010 [Retreived on Jan. 22, 2010].*
[Retreived from]:http://www.rush.edu/rumc/page-1203344434680.html, 4 pages, 2010 [Retreived on Jan. 22, 2010].*
Uemura 2002, Circ. J., 66, 1155-1160.*
Nevin, et al., Pharmocology and Therapeutics, 2002, 95, 59-293.*
Nathan et al., "Nitric oxide synthases: roles, tolls, and controls," Cell (1994) 78:915-918.
Palmer, R. M., et al., "Nitric oxide release accounts for the biological activity of endothelium-derived relaxing factor," Nature (1987) 327:524-526.
Yamada, M., et al., "Edothelial nitric oxide synthase-dependent cerebral blood flow augmentation by L-arginine after chronic statin treatment," (2000) 20(4):709-17.
Harrison, David G., "Cellular and modecular mechanisms of endothelial cell dysfunction," J. Clin. Invest. (1997) 100(9):2153-2157.
Wu, Guoyao and Morris, Sidney M., "Arginine metabolism: nitric oxide and beyond," Biochem. J. (1998) 366:1-17.
Morris, Sidney M. and Billiar, Timothy R., "New insights into the regulation of inductible nitric oxide synthesis," Am. J. Physiol. (1994) 266:E829-E839.
Dhanakoti, et al., "Renal arginine synthesis: studies in vitro and in vivo," Am. J. Physiol. (1990) 253:E437-442.
Kown, M., et al., "L-arginine polymers inhibit the development of vein graft neointimal hyperplasia," J. Thoras. Cardiovasc. Surg. (2001) 121(5):971-980.
Uemura, S., et al., "Rapid and efficient vascular transport of arginie polymers inhibits myointimal hyperplasia," Circulation (2000) 102: 2629-2635.
Kown, Murray H., et al., "L-arginine polymer mediated inhibition of graft coronary artery disease after cardiac transplantation," Transplantation (2001) 71(11):1542-1548.
Mitchell, D. J., "Polyarginine enters cells more efficiently than other polycationic homopolymers," J. Peptide Res. (2000) 56:318-325.

* cited by examiner

*Primary Examiner*—Andrew D Kosar
*Assistant Examiner*—Satyanarayana R Gudibande
(74) *Attorney, Agent, or Firm*—McKinney Law Group; Jeffrey A. McKinney

(57) ABSTRACT

This invention relates to compositions and methods for treatment of vascular conditions. The invention provides arginine polymers and arginine homopolymers for the treatment and/or prevention of glaucoma, pulmonary hypertension, asthma, chronic obstructive pulmonary disease, erectile dysfunction, Raynaud's syndrome, heparin overdose, vulvodynia, and wound healing. The invention also provides arginine polymers and arginine homopolymers for use in organ perfusate and preservation solutions.

5 Claims, No Drawings

COMPOSITIONS AND METHODS FOR TREATING DISEASES

CROSS REFERENCE TO RELATED APPLICATION

This application is a continuation of application Ser. No. 11/736,689 filed on Apr. 18, 2007, now U.S. Pat. No. 7,557,087 which is a continuation of application Ser. No. 11/070,528 filed on Mar. 1, 2005 now abandoned which claims priority to U.S. Provisional Application No. 60/549,321, filed Mar. 1, 2004 and which is hereby incorporated by reference.

BACKGROUND OF THE INVENTION

Numerous vascular conditions afflict mammals. Such conditions include, but are not limited to, coronary and peripheral arterial diseases, chronic rejection, vasculopathy associated with diabetes, pulmonary vascular conditions (e.g., pulmonary arterial hypertension and chronic obstructive pulmonary disease), ocular vascular conditions (e.g., intraocular pressure and glaucoma), sexual dysfunction vascular conditions (e.g., erectile dysfunction and vulvodynia), and dermal vascular conditions (e.g., Raynaud's phenomenon, scleroderma and wound healing).

A known compound that has a general dilatory effect on the vascular system is nitric oxide (NO). See Nathan et al., Cell (1994) 78:915-916. NO plays an essential role in mammalian physiology and is responsible for various functions including vascular tone, endothelium dependent reactions, activation of soluble guanylate cyclase, neurotransmission in the central and peripheral nervous systems, and activated macrophage cytotoxicity. In particular, as the endothelial-derived relaxation factor (EDRF), NO plays a crucial role in vasodilation throughout the body and is a known antagonist of endothelin-1, one of the most potent mammalian vasoconstrictors. See Palmer, R. M., et al., Nature (1987) 327:524-526. It is believed that NO functions by binding to heme and activating soluble guanylate cyclase to increase the cellular content of cGMP and activate cGMP-dependent protein kinases. The latter both generate vasodilatory effects and reduce blood vessel tone. Other functions of NO include the inhibition of platelet adherence and aggregation, and the inhibition of vascular smooth muscle proliferation and leukocyte adherence. Thus, NO is considered an inhibitor of stenosis, restenosis, vascular inflammation, vascular cell proliferation, thrombosis, atherosclerosis, and arteriosclerosis.

NO is synthesized, at least in part, from L-arginine by a family of enzymes known as nitric oxide synthases (NOS). It is believed that NOS converts L-arginine, NADPH, and oxygen into citrulline, NADH, and NO. NOS occur in several isoforms: an endothelial nitric oxide synthase (eNOS), a machrophage or inducible nitric oxide synthase (iNOS), and a neuronal nitric oxide synthase (nNOS). Unlike its name, eNOS has been detected not only in endothelial cells and blood vessels, but also in epithelium of tissues including, but not limited to, bronchial cells and neurons of the brain, especially in the pyramidal cells of the hippocampus. Furthermore, iNOS has been detected not only in macrophages but also in cells such as hepatocytes, chrondrocytes, endothelial cells, and fibroblasts, in particular under conditions of endothelial damage or as part of a response to injury.

The NOS isoforms can also be categorized as either constitutive or inducible. Constitutive NOS (cNOS) include eNOS and nNOS, while iNOS is inducible. cNOS are usually present in a cell, but remain inactive until intracellular calcium levels increase resulting in enhanced calcium/calmodulin binding and subsequent activation. Unlike cNOS, iNOS is calcium independent and is not normally present in cells. However, iNOS can be induced by lipopolysaccharides and certain cytokines. It is postulated that cytokine activity affects gene expression/splicing, mRNA stability, and protein synthesis, resulting in iNOS. It is also expected that the induced form of NOS produces a much greater amount of NO than cNOS, and may even result in toxicity when the L-arginine supply is limited. Induction of iNOS can be inhibited by gluococorticoids and some cytokines.

Recent studies suggest that NOS inhibitors may be associated with endothelial vasodilator dysfunction. In particular, asymmetric dimethylarginine (ADMA), and to a lesser extent, N-monomethylarginine (NMA) are associated with endothelial vasodilator dysfunction. Patients with coronary and peripheral arterial disease and those with renal failure have greater amounts of plasma ADMA. However, it has been shown that while exogenous ADMA vasoconstricts vascular rings in vitro, the vasoconstriction effect can be reversed by L-arginine.

Formation of NO by eNOS is thought to play an important role in normal blood pressure regulation, prevention of endothelial dysfunction such as hyperlipodemia, arteriosclerosis, atherosclerosis, thrombosis, restenosis, ischemia, and apoptosis. eNOS is the predominant synthase present in brain and endothelium and may be active under basal conditions. Yamada M., J. Cereb. Blood Flow Metab. (2000) April; 20(4): 709-17. eNOS can be stimulated by increases in intracellular calcium that occur in response to receptor-mediated agonists or calcium ionophores. Studies further suggest that cNOS activity can be regulated by a negative feedback manner by NO.

Since intracellular levels of L-arginine are normally greater that NOS enzyme, NO syntheses generally do not depend on extracellular supplementation. See Harrison, D. G., et al. J. Clin. Invest. (1997) 100:2153-2157. However, under certain circumstances, local L-arginine concentrations might become rate limiting. Such circumstances might include local tissue inflammation, elevated plasma or tissue levels of ADMA; inflammation-induced expression of the iNOS; increased expression of arginase, and presence of iNOS stimulants such as IFN-γ and LPS. See Guoyao, et al. Biochem. J. (1998) 366:1-17.

As a free radical gas, NO has an extremely short half-life. See Morris et al., Am. J. Physiol. (1994) 266:E829-E839. Thus, it is desired to increase the effective amount of NO in a cell, tissue, and/or organ in order to induce vascular relaxation, dilation, or vascularization, and oxygenation, and other NO mediated biological processes. Previous publications suggest that NO can be increased by administering to an organism a NO donor that releases NO, e.g., glyceryl trinitrate, isosorbide 5-mononitrate, isosorbide dinitrate, pentaerythritol, pentaerythritol tetranitrate, etc. One of the greatest limitations in administering a NO donor is that in vivo administration of such compounds can induce severe systemic hypotension. See Heros et al., Surgical Neurology, (1976) 5:354-362. Others have suggested that L-arginine monomers can be administered to prevent vasoconstriction and vascular conditions such as atherosclerosis and restenosis. See Cooke et al., U.S. Pat. No. 5,428,070. L-arginine is taken up by cells by way of the y+ transporter. This transport mechanism is limited according to the expression of the transporter and other molecules competing for the transporter (including ADMA).

Therefore, it is desirable to find new compositions and methods for treating and/or preventing vascular conditions or to increase the local tissue concentration of NO without causing clinically significant systemic hypotension.

SUMMARY OF THE INVENTION

The present invention provides methods for treatment and prevention of vascular conditions or local tissue NO deficiencies by administering a therapeutically effective amount of a NO enhancer. A NO enhancer is any composition that increases the metabolic or enzymatic production of NO by NOS. In preferred embodiments, a NO enhancer is any composition that increases the metabolic or enzymatic production of NO by cNOS. More preferably a NO enhancer is any composition that increases the metabolic or enzymatic production of NO by iNOS. A NO enhancer does not generally contain, release, or donate a nitric-oxide moiety (e.g., glyceryl trinitrate). Instead, a NO enhancer can be, for example, an arginine polymer or copolymer, or more preferably an arginine homopolymer.

An arginine polymer refers to a composition wherein arginine is a major component. An arginine polymer or copolymer preferably comprises of about 2-500 arginine residues, more preferably 3-400 arginine residues, more preferably 4-300 arginine residues, more preferably 5-200 arginine residues, more preferably 6-100 arginine residues, more preferably 7-50 arginine residues, more preferably 8-40 arginine residues, or more preferably 9-30 arginine residues. Preferably at least 50% of the residues of an arginine polymer or copolymer are arginine, more preferably at least 60% of the residues of an arginine polymer or copolymer are arginine, more preferably at least 70% of the residues of an arginine polymer or copolymer are arginine, more preferably at least 80% of the residues of an arginine polymer or copolymer are arginine, or more preferably at least 90% of the residues of an arginine polymer or copolymer are arginine.

In preferred embodiments, the NO enhancer is an arginine homopolymer, consisting of arginine residues. An arginine homopolymer can consist of L-arginine residues, D-arginine residues, or a combination of L- and D-arginine residues. Preferably, an arginine homopolymer consists of L-arginine residues. The compositions herein are preferably formulated for local delivery (e.g., by topical applications or by microinjection). Particular vascular conditions that are treatable and/or preventable by the composition herein include coronary and peripheral arterial diseases, chronic rejection, vasculopathy associated with diabetes, scleroderma, glaucoma, pulmonary hypertension, chronic obstructive pulmonary disease, wound healing, anal fissures, vulvodynia, erectile dysfunction, Raynaud's phenomenon, and heparin overdose. The compositions herein are also useful in perfusate solutions for the preservation and perfusion of organs either alone or in combination as an additive to standard perfusates.

DETAILED DESCRIPTION OF THE INVENTION

I. Compositions

The term "amino acid" or "residue" as used herein includes any one of the twenty naturally-occurring amino acids, the D-form of any one of the naturally-occurring amino acids, non-naturally occurring amino acids, and derivatives, analogs and mimetics thereof. Any amino acid, including naturally occurring amino acids, may be purchased commercially or synthesized by methods known in the art. Examples of non-naturally-occurring amino acids include norleucine ("Nle"), norvaline ("Nva"), β-Alanine, L- or D-naphthalanine, ornithine ("Orn"), homoarginine (homoArg) and others well known in the peptide art, including those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference.

Common amino acids may be referred to by their full name, standard single-letter notation, or standard three-letter notation for example: A, Ala, alanine; C, Cys, cysteine; D, Asp, aspartic; E, Glu, glutamic acid; F, Phe, phenylalanine; G, Gly, glycine; H, His, histidine; I, Ile isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine. Any and all of the amino acids in the compositions herein can be naturally occurring, synthetic, and derivatives or mimetics thereof.

The present invention relates to compositions for the treatment of vascular conditions by increasing the effective amount of NO. The effective amount of NO is increased preferably by increasing the metabolic or enzymatic production of NO. Compositions that effectively increase the amount of NO by increasing the metabolic or enzymatic production of NO are referred to herein as "NO enhancers." In preferred embodiments, a NO enhancer is a composition that increases the effective amount of NO produced by NOS. More preferably, a NO enhancer is a composition that increases the effective amount of NO produced by cNOS, especially eNOS. In other preferred embodiments, a NO enhancer is a composition that increases the effective amount of NO produced by iNOS. If not specified, a NO enhancer is a composition that increases the effective amount of NO produced by both the constitutive and inducible forms of NOS. It is further contemplated by the present invention that the metabolic or enzymatic production of NO can be increased by increasing the effective amount of a NO precursor, e.g., L-arginine, in a cell, tissue or organ. Therefore, any composition that enhances the effective amount of a NO precursor is a NO enhancer. In preferred embodiments, a NO enhancer is comprised of L-arginine linked to a delivery mechanism that increases the rate of L-arginine transport across a cell membrane. In some preferred embodiments, the NO enhancer is an arginine polymer or an arginine homopolymer as further described herein.

A NO enhancer of the present invention does not contain a NO moiety that is donated or released, as described in e.g. U.S. Pat. Nos. 5,873,359, 6,156,975, and 6,358,536. Examples of NO enhancers include precursors of the NOS metabolic pathway, or more preferably the iNOS metabolic pathway, and substrates or precursors of the above. It is contemplated by the present invention that NOS generate NO by converting L-arginine into NO by an enzymatic reaction. It is further contemplated that iNOS generates NO by converting L-arginine into NO by an enzymatic reaction, in particular, in response to vascular stress or injury. Thus, in preferred embodiments, a NO enhancer is any composition that increases the effective amount of arginine, or more preferably L-arginine, in a cell, tissue or organ. Such compositions include substrates and precursors in the arginine synthesis pathway (e.g., citrulline or lysine) (Dhanakoti, *Am. J. Physiol.* (1990) 253:E437-42), as well as arginine polymers, copolymers and homopolymers. The term arginine polymer includes arginine copolymers and arginine homopolymers.

An arginine polymer or copolymer includes an oligomer containing preferably 2-500 amino acids in length, more preferably 3-400 amino acids in length, more preferably 4-300 amino acids in length, more preferably 5-200 amino acids in length, more preferably 6-100 amino acids in lengths, more preferably 7-50 amino acids in lengths, or more preferably 8-30 amino acids in length.

Preferably, at least 50%, more preferably at least 60%, more preferably at least 70%, more preferably at least 80%, more preferably at least 90% of the amino acid residues of an arginine polymer or copolymer are arginine residues.

In preferred embodiments, an arginine polymer or copolymer includes at least 3 contiguous arginine residues, more preferably at least 4 contiguous arginine residues, more preferably at least 5 contiguous arginine residues, more preferably at least 6 contiguous arginine residues, more preferably at least 7 contiguous arginine residues, more preferably at least 8 contiguous arginine residues, more preferably at least 9 contiguous arginine residues, and more preferably at least 10 contiguous arginine residues. In some embodiments, an arginine polymer or copolymer includes about 3 to about 100 contiguous arginine residues, more preferably about 6 to about 50 contiguous arginine residues, more preferably about 7 to about 30 contiguous arginine residues, and more preferably about 8 to about 20 contiguous arginine residues.

The contiguous arginine residues can be at the C-terminus of the polypeptide, N-terminus of the polypeptide or in the center of the polypeptide (e.g., surrounded by non-arginine amino acid residues). Non-arginine residues are preferably amino acids, amino acid derivatives, or amino acid mimetics that do not significantly reduce the rate of membrane transport of the polymer into cells, including, for example, glycine, alanine, cysteine, valine, leucine, isoleucine, methionine, serine, threonine, α-amino-beta-guanidinopropionic acid, α-amino-γ-guanidinobutyric acid, and α-amino-ε-guanidinocaproic acid. In preferred embodiments, the arginine polymer does not include lysine and histidine monomers.

In some embodiments, an arginine polymer can be attached to one or more backbone. A backbone can be any structure that allows for the attachment of one or more NO enhancers, arginine polymers, arginine copolymers, and/or arginine homopolymers. The NO enhancers, arginine polymers, copolymer and/or homopolymers can be attached to the backbone covalently or non-covalently, directly or by a linker arm. The backbone can be composed of monomer units that are covalently and/or non-covalently linked. Examples of covalent backbones include oligosaccharides, peptides, lipids and other cross-linked monomers. Examples of non-covalent backbones include liposomes, micelles, colloids, protein aggregates, modified cells, and modified viral particles. The backbone can form any structure, including but not limited to, linear, branched, hyperbranched, dendrimer, block, star, graft, derivatized, liposomes, michelles, and colloids. In preferred embodiments, one or more arginine polymers, copolymers, or homopolymers are attached to a backbone (e.g., oligosaccharide) by an ester linkage. In other preferred embodiments, the backbone may be a liposome or a micelle that presents on its surface one or more arginine polymers, copolymers, or homopolymers.

The length and composition of the polymers and backbones can be designed to control the rate of transport of the polymer into cells, tissues, and organs. For example, it has been demonstrated that shorter polyarginine (e.g., r7 or R7 (Seq. ID No. 1)) have the ability to translocate across vascular cells using a mechanism independent of known amino acid transport systems. See Uemura, S., et al., Circ. J. (2002) December; 66 (12):1155-60; Kown, M H, et al., Transplantation (2001) June 15; 71(11):1542-8; U.S. Pat. Nos. 6,495,663 and 6,593,292. Thus, in preferred embodiments, the length of the arginine polymer or copolymer can vary depending upon its desired rate of translocation. For example, for quick translocation a composition can comprise of for example, 6-30 contiguous arginines, more preferably 7-25 contiguous arginines, more preferably 8-20 contiguous arginines, or more preferably 9-15 contiguous arginines. For a slower translocation, the number of arginine residues or contiguous arginine residues can be adjusted (e.g., about 10-700 contiguous arginine residues, more preferably about 20-600 contiguous arginine residues, more preferably about 30-500 contiguous arginine residues, more preferably about 40-400 contiguous arginine residues, more preferably 50-300 contiguous arginine residue, more preferably 60-200 contiguous arginine residues, and more preferably 70-100 contiguous arginine residues).

An arginine polymer can include L-arginines, D-arginines, or a combination of both L and D-arginines. Generally, the term "polyarginine" as used herein refers to a polymeric sequence of contiguous arginine residues. The term "poly-L-arginine" refers to a polymeric sequence composed of all L-arginines. The term "poly-D-arginine" refers to a polymeric sequence composed of all D-arginines. The term "poly-L-arginine" may be abbreviated by an upper case "R" followed by the number of L-arginine in the peptide (e.g., R9 (SEQ. ID NO. 2) represents a 9-mer of contiguous L-arginine residues). The term "poly-D-arginine" may be abbreviated by the lower case "r" followed by the number of D-arginines in the peptide (e.g., r9 (SEQ. ID NO. 2) represents a 9-mer of contiguous D-arginine residues). "Ac" indicates a sequence having an acetylated N-terminal residue (e.g., AcR9), while "b" indicates a sequence having a biotinylated N-terminal residue (e.g., bR9).

In preferred embodiments, an arginine polymer or copolymer comprise at least 50% L-arginine residues, more preferably at least 60% L-arginine residues, more preferably at least 70% L-arginine residues, more preferably at least 80% L-arginine residues, more preferably at least 90% of L-arginine residues, or more preferably all L-arginine residues.

When a polymer comprises of only arginine residues, it can be referred to herein as an "arginine homopolymer." An arginine homopolymer can contain a mixture of L-arginine and D-arginine residues, or a combination of L- and D-arginine residues. Preferably at least 50% of all arginine residues in an arginine homopolymer are L-arginine, more preferably at least 60% of all arginine residues in an arginine homopolymer are L-arginine, more preferably at least 70% of all arginine residues in an arginine homopolymer are L-arginine, more preferably at least 80% of all arginine residues in an arginine homopolymer are L-arginine, more preferably at least 90% of all arginine residues in an arginine homopolymer are L-arginine, and more preferably all arginine residues in an arginine homopolymer are L-arginine.

Arginine homopolymers are preferably 2-500 amino acids in length, more preferably 3-400 amino acids in length, more preferably 4-300 amino acids in length, more preferably 5-200 amino acids in length, more preferably 6-100 amino acids in lengths, more preferably 7-50 amino acids in lengths, more preferably 8-40 amino acids in lengths, or more preferably 9-30 amino acids in length.

In any of the polymers herein, the terminal ends can be either capped or uncapped. Preferably, the terminal ends of the arginine polymers are uncapped, such that the terminal amino and carboxylic acid group are free. However, capping is appropriate if it does not reduce the therapeutic affect of the composition (e.g., reduce the level of NO production). Examples of N-terminal caps include: N-acetyl, N-methyl, N-dimethyl, N-ethyl, N-diethyl, N-Boc, N-benzyl group, etc. Examples of C-terminal caps include an amino group of the form $NR_2$ (e.g., free amino, alkylamino, or dialkylamino) to form a terminal amide moiety ($CONR_2$), wherein each R group is separately H, or a linear, cyclic or branched $C_1$-$C_{10}$ alkyl group, preferably $C_1$-$C_5$ alkyl, and more preferably $C_1$-$C_2$ alkyl); or an alkyl alcohol of the form OR, to form a carboxylic acid ester ($CO_2R$), wherein R is linear, cyclic or branched $C_1$-$C_{10}$ alkyl group, preferably $C_1$-$C_5$ alkyl, and more preferably $C_1$-$C_2$ alkyl, or the like. Preferably, such N- and C-capping groups contain no more than 20 carbon atoms, and preferably no more than 10 carbon atoms.

In some embodiments, a polymer herein has a formula X-$Arg_n$-Y, wherein X is $NH_2$ or an N-terminal capping group, Y is $COO^-$ or a C-terminal capping group, and n is an integer from 2-500, more preferably from 3-400, more preferably from 4-300, more preferably from 5-200, more preferably from 6-100, more preferably from 7-50, more preferably from 8-40, or more preferably from 9-30.

Preferably, the compositions herein, e.g., arginine polymers, have enhanced translocation abilities. Homopolymers or peptides containing a high percentage of cationic amino acid residues have been shown to have a higher ability to cross the plasma membrane of cells. See Mitchell D J., et al., *J. Peptide Res.*, (2000) 56, 318-325. Various translocation abilities of arginine polymers and other cationic polymers have been discussed in D. J. Mitchell, et al., *J. Petide. Res.*, (2000) 56, 318-325; Kown, M H, et al., *Transplantation*, (2001) Jun. 15; 71(11):1542-8; Kown, M. et al., *J. Thorac. Cardiovasc. Surg.*, (2001) May; 121(5):971-80; Uemura, S., et al., *Circ J.*, (2002) December; 66(12):1155-60; and Uemura, S., et al., *Circulation*, (2000) 102; 2629-2635. In Preferred embodiments, R5-R12, more preferably R6-R11, more preferable R7-R10, and more preferably R8 or R9 are used to treat and/or prevent vascular conditions.

In any of the embodiments herein, the stereochemistry of amino acids can be altered to control the stability of a polymer. In general, D-isomers are more resistant to endogenous protease and therefore have a longer half-life than L-isomers. On the other hand, L-isomers are more susceptible to protease activity and degrade more readily into L-arginine monomers. Therefore, a R9 polymer will degrade more readily than a r9 polymer and, as a NO enhancer, may increase NO levels in a cell, tissue, organ, or organism faster. Thus, the compositions herein can be adjusted for quick release or slow release by altering the stereochemistry of the arginines.

As discussed above, the amino acids and polypeptides herein can be naturally occurring or synthetic. Amino acids and peptides can be produced using techniques that are well known in the art, including chemical synthesis techniques and recombinant DNA techniques. The production of peptides using recombinant DNA techniques is described, for example, in U.S. Pat. No. 5,593,866. Chemical synthesis of peptides can be accomplished using techniques that are well known in the art, such as TBOC or FMOC protection of alpha-amino groups. See Coligan, et al., *Current Protocols in Immunology*, (Wiley Interscience Unit 9, 1991). Peptides of the invention can also be synthesized by the well-known solid phase peptide synthesis methods. See Merrifield, J. Am. Chem. Soc., (1962) 85:2149; Stewart and Young, Solid Phase Peptide Synthesis (Freeman, San Francisco, 1969) pp. 27-62. These and all other references and publication described in this application are incorporated herein by reference for all purposes.

Non-peptide compounds that mimic the function of peptides herein can also be employed in conjunction with this invention. Such peptide mimetics can be produced as described, for example, by Saragovi et al., *Science* (1991) 253:792-95. Peptide mimetics are molecules which mimic elements of protein secondary structure. See, e.g., Pezzuto et al., Eds., (Chapman and Hall, New York 1993). The underlying rationale behind the use of peptide mimetics is that the peptide backbone of proteins exists chiefly to orient amino acid side chains in such a way as to facilitate molecular interactions. For the purposes of the present invention, appropriate peptide mimetics are considered to be the equivalent of the peptides herein.

II. Indications for Use

The compositions herein can be used for treatment and/or prevention of all vascular conditions afflicting mammals. Common vascular conditions afflicting mammals include but are not limited to, acute thrombotic occlusion, aneurysm, aortoiliac and lower occlusive arterial disease, arterial occlusion, arteriosclerosis atherosclerosis, brachiocephalic and upper extremity occlusive disease, Behcet's Syndrome, carotid artery disease, chronic rejection, vasculopathy associated with diabetes, clogged arteries, degos, dementia, early embolic stroke, headaches, hemorrhoids, heparin overdose, hereditary angioedema, intracoronary thrombus, intimal hyperplasia, ischemia, lymphedema, myoamoya, myocardial infraction, myointimal hyperplasia, peripheral arterial disease (PAD), pseudoxanthoma elasticum, restenosis sclerosis, scleroderma, stenosis thoracic outlet syndrome, thromboangiitis obliterans, thrombosis, varicose veins, vasculitis, and venous and lymphatic disease.

In one example, the compositions herein can be administered for the treatment of heparin overdose. In general, heparin inhibits blood clotting and the formation of fibrin clots both in vitro and in vivo. Heparin acts at multiple sites in the vascular system. Small amounts of heparin sodium in combination with antithrombin III (heparin cofactor) can inhibit thrombosis by inactivating activated Factor X and inhibiting the conversion of prothrombin to thrombin. Once active thrombosis has developed, larger amounts of heparin sodium can inhibit further coagulation by inactivating thrombin and preventing the conversion of fibrinogen to fibrin. Heparin sodium can also prevent the formation of a stable fibrin clot by inhibiting the activation of the fibrin stabilizing factor.

Currently, compounds available for the treatment of heparin overdose include protamine sulfate. See U.S. Pat. No. 5,919,761 (incorporated herein by reference for all purposes) (disclosing a prevalent salmine protamine peptide having 32 amino acid residues with 67% of the total sequence being arginine and having an arginine 6-mer). Protamine sulfate, however, has numerous negative side effects including, hypotension, bradycardia, pulmonary artery hypotension, depressed oxygen consumption, thrombocytopenia with pulmonary platelet sequestration, and leukopenia.

The present invention contemplates the use of NO enhancers, or more preferably arginine polymers, or more preferably arginine homopolymers, to neutralize heparin in treating heparin overdose. In particular, arginine polymers comprising of 70% or more arginine residues are contemplated. In preferred embodiments at least 7, or more preferably at least 8, or more preferably at least 9 contiguous arginine residues are included in the arginine polymer. It is also preferred that the contiguous arginine residues be L-arginine.

In some embodiments, arginine homopolymers are used for the treatment of heparin overdose. The arginine homopolymers are preferably 8-40 amino acids in length or more preferable 9-30 amino acids in length. NO enhancers used for the treatment of heparin overdose are preferably formulated for oral or intravenous administration. The NO enhancers may be administered independently or co-administered with additional therapeutic agents such as natural protamine sulfate.

In another example, the present invention contemplates the use of NO enhancers, more preferably arginine polymers, or more preferably arginine homopolymers, for organ transport and perfusate solutions. Such solutions can be used, for example, for organ storage and delivery and for organ flushing (e.g., quick wash of organs that does not require storage). Perfusate solutions that are used for quick organ flushing can preserve organ function, maintain cellular function, and decrease chronic rejection.

Currently, the largest single unresolved problem in organ transplantation and organ reperfusion is failure of the blood vessels. Endothelial cells form the vascular lining and are sensitive to changes in environmental conditions. When an organ is harvested cellular deterioration begins immediately and eventually damages the organ. Preservation solutions can extend the period of time that an organ remains viable for transplant after it is removed from a donor. That period may vary between different organs depending on different limitations in each organ. For example, with today's technology, hearts and lungs can be preserved safely for about 4-6 hours; livers can be preserved for about 12-18 hours; and kidneys can be preserved for about 24 hours. Preservative solutions can also be used to decrease the likelihood that a patient receiving an organ will experience post-operative vascular conditions, including but not limited to, atherosclerosis, restenosis, transplant arteriosclerosis, stenosis, and ischemia.

Numerous preservative solutions have been developed and used to preserve major organs while they are in cold storage prior to their transplantation. A preservative solution or perfusate solution contains a variety of compounds that act as osmotic agents to prevent cell swelling thereby protecting organs from swelling associated cellular necrosis during storage. The invention herein contemplates the use of NO enhancers, more preferably arginine polymers, and more preferably arginine homopolymers in preservative solutions and/or perfusate solutions. The preservative solutions contemplated by the present invention include all those known in the art.

For example, two widely used preservative flush solutions which are commercially available are the Collins (Collins G. M., *The Lancet*, (1969) 1219-1222) and the Euro-Collins (Squifflet, J. P., et al., *Transplant. Proc.*, (1981) 13:693-696) solutions. These solutions resemble intracellular fluid and contain glucose as an osmotic agent. However, despite their widespread use, the Collins and Euro-Collins preservative solutions do not provide adequate preservation for storage time greater than about 48 hours.

Higher osmolality preservative solutions have been prepared using, for example, raffinose and lactobionate in the University of Wisconsin solution ("UW solution") (Ploeg R. J., et al, *Transplant. Proc.*, (1988) 20 (suppl. 1) 1:935-938); mannitol in the Sacks solution (Sacks S. A., *The Lancet*, (1973) 1:1024-1028), sucrose in the phosphate buffered sucrose (PBS) preservative solution (Lam, F. T., et al, *Transplantation*, (1989) 47:767-771) and the histidine buffered HTK solution of Bretschneider (Kallerhoff, N. M., et al, *Transplantation*, (1985) 39:485-489). Hypertonic citrate preservative solutions are also known (H. Ross et al, *Transplantation*, (1976) 21:498-501). However, these solutions are unable to extend the preservation of organs beyond about 72 hours using cold storage methods.

The UW solution, which is described in more detail in U.S. Pat. Nos. 4,879,283 and 4,798,824, incorporated herein by reference for all purposes, includes roughly 5% by weight hydroxyethyl starch with molecular weight ranging between 150,000-350,000 Daltons and an osmolality level of about 320 mOsm/liter. Other agents in the UW solution include, optionally, lactobionate salt, raffinose, electrolytes, glutathione, potassium phosphate, magnesium gluconate, adenosine, insulin, bactrim, dexamethasone, allopurinaol and other anti-inflammatory, antibiotic, anti-metabolic, and anti-neoplastic agents. Any of the above compounds may be used in a preservation solution to prevent cell swelling or leakage which can damage the stored organ. However, the UW solution contains relatively minor buffering capacity such that during initial flushing the high pressure may induce vasoconstriction and endothelial damage, because of its high potassium content and high viscosity. See Mohara J., *J. Heart Lung Transplant.*, (2002) March; 21(3):383-90.

The Bretschneider HTK solution is substantially less viscous than the UW solution, has higher concentrations of histidine, tryptophane, and agr-ketoglutarate, and contains less potassium. Furthermore, the HTK solution, unlike the UW solution, does not need to be stored in cold temperature and requires no additional products prior to use.

Other known preservation solutions include those disclosed in U.S. Pat. Nos. 4,873,230; 6,492,103; and 6,544,726, as well as U.S. Application Serial Nos. 2002/0051779; 2002/0090369; 2002/0132220; and 2003/0118980, all of which are incorporated herein by reference for all purposes.

Thus, it is contemplated by the present invention that a solution comprising a therapeutically effective amount of a NO enhancer can be used as an organ transport or perfusate solution. In preferred embodiments, the NO enhancer is an arginine polymer, and more preferably an arginine homopolymer. The NO enhancer(s) can be formulated as a solution or as a powder that easily dissolves into a solution.

The perfusate solutions of the present invention may optionally include 1-10% by weight hydroxyethyl starch. The perfusates of the present invention may have a molecular weight ranging between 50,000-700,000 Daltons, more preferably 150,000-600,000 Daltons, more preferably 250,000-500,000 Daltons, or more preferably 350,000-400,000 Daltons. Preferably, the perfusates herein have an osmolality level ranging between 50,000-700,000 mOsm/liter, more preferably 150,000-600,000 mOsm/liter, more preferably 250,000-500,000 mOsm/liter, or more preferably 350,000-400,000 mOsm/liter.

The NO enhancer preservation solutions can optionally comprise one or more additional agents. Such agents can, for example, modulate osmolality, reduce post-operative restenosis or atherosclerosis, or reduce cell atrophy after harvesting but before transplant. Examples of additional agents include, but are not limited to, hyroxyethyl starch, lactobionic acid, gluconate, sodium gluconate, magnesium gluconate, dextran, sucrose, hypoxanthine, a glucocorticoid, a non-glucocorticoid lazaroid, tetracycline, pentoxyphyline, calcium chloride, penicillin, insulin, dexamethasone, glutathione, glucose, potassium phosphate, phosphate, adenosisne, allopurinol, dbcyclic AMP, trehalose, nitroglycerin or any other agents known in the art of preparation for preservation solutions.

The perfusate solutions herein may be administered to an organ before harvesting, during transport, or after transplant. Thus the transported perfusate solutions may be applied both in vivo and ex vivo to organs being transplanted.

The invention herein also contemplates the use of NO enhancer(s) for the treatment of chronic rejection, vasculopathy, or other complications associated with type-1 diabetes. Type-1 diabetes, also known as insulin-dependent diabetes mellitus or juvenile diabetes, occurs when the immune system fights against the body's own insulin-producing islet cells in the pancreas leading to the eventual destruction of such cells. Without the islet cells, the pancreas produces little or no insulin. Type-1 diabetes accounts for 5-10% of all diabetes cases in the Unites States and often results in vascular complications and/or nerve damage that can affect any organ in the body, including, but not limited to the eyes, kidneys, and heart.

Vascular complications associated with type-1 diabetes include stenosis, angiopathy, high blood pressure, heart attacks, strokes, heart failure, hypertension, and kidney damage. It is thought that type-1 diabetes may accelerate the progression of atherosclerosis (hardening of the arteries), which can further lead to coronary artery disease, heart attacks, and strokes. In fact, heart attacks and strokes account for about 60% and 25% of all deaths in diabetics, respectively. In particular, microangiopathy occurs in many diabetics. Microangiopathy refers to the thickening of the walls of small blood vessels. Angiopathy can cause small blood vessels to bleed, leak protein, and slow the flow of blood through the body. When cells downstream from an angiopathic site (e.g., ocular cells) do not receive enough blood, they become damaged.

Nerve damage, or neuropathy, associated with type-1 diabetes also causes major complications that can affect the entire body. For example, nerves that connect the spinal cord, muscles, skin, blood vessels, and other organs may become damaged due to diabetes. Particularly severe is nerve damage affecting the heart. Other vascular and neurological conditions that affect diabetics include foot problem and foot pain that develops from complications in blood vessels and in the peripheral nervous system. Such complications may result in changes to both bone structure and soft tissue structure in the feet of diabetics. It may also cause foot ulcers that are difficult to cure. Overall changes in bone structure can also lead to increase osteoporosis.

Type 1 diabetes is also the leading cause of new cases of blindness in adults, accounting for approximately 12,000 to 24,000 new cases of blindness annually. Blindness is usually the result of retinopathy. Other eye disorders that affect diabetics and which may result in blindness include cataracts and glaucoma. Diabetics also face a greater risk of suffering from complications associated with influenza or pneumonia causing pulmonary hypertension and other pulmonary vascular conditions. It is also estimated that diabetics are twice as likely to suffer from depression as non-diabetics.

Thus, the present invention contemplates the use of NO enhancers, more preferably arginine polymers, or more preferably arginine homopolymers, for the treatment of vasculopathy and/or other complications associated with type-1 diabetes. Such conditions include, but are not limited to, glaucoma, foot ulcers, angina, myocardial infraction, and post ischemia. The NO enhancer(s) are preferably delivered locally to a site of stenosis or microangiopathy (e.g., in kidney arteries, coronary arteries, foot ulcers, etc.). Delivery may be made by catheter (e.g., a Dispatch™ catheter), microinjection, or other localized delivery system. The compositions are formulated according to the route of administration and may include additional therapeutic agents.

The present invention also contemplates the use of NO enhancers for the treatment and prevention of vascular conditions associated with vein grafting, e.g., graft coronary artery disease and graft peripheral artery disease. The terms "graft," "vessel," "conduit," and "segment" are used interchangeably herein to refer to any full-length or partial segment of a conduit, whether naturally occurring or synthetic that that may be grafted to bypass an obstruction in the vascular system or to increase blood flow to a particular region in the vascular system. Exemplary uses of vein grafting include: coronary artery bypass grafting (CABG), peripheral artery bypass grafting (PABG), and venous-arterial grafting (VAG).

Currently, CABG is the most commonly performed "open heart" operation in the United States. CABG is a procedure performed to bypass blockage(s) or obstruction(s) of the coronary arteries. The coronary arteries are the blood vessels that supply blood and fuel to the heart. Ischemia refers to a condition where the heart does not get enough fuel, such as when the coronary artery is blocked or occluded. Ischemia can cause muscle atrophy leading to heart attacks.

When there is blockage in the artery, an individual may experience chest pain. Traditional CABG techniques to treat coronary artery blockage involved grafting a portion of the saphenous vein from the leg into the heart to carry blood around the obstruction. At one end the saphenous vein was attached to the aorta, and at the other end the saphenous vein was attached to the coronary artery beyond the blockage. Recently, surgeons discovered that an artery from the inside of the chest wall (the internal thoracic artery or internal mammary artery) could also be used as a vein graft for CABG. Other arteries and veins may also be used for CABG, including, for example, the gastroepiploic artery.

In performing a CABG procedure, it is preferable that the implanted vein or artery segment be autologous, or from the same individual. However, venous and arterial segments from other human donors can also be used. Such segments are referred to herein as allograft segments. Segments may also be obtains from other animals, e.g., pigs, and are referred to herein as xenografts. In addition, a vessel conduit provided for a CABG procedure may be an artificial vessel made from a physiologically compatible material, e.g., "DACRON"™, PTFE, or other non-tissue graft material. An artificial vessel is preferably prepared or derivatized, e.g., by carboxylation, sulfonation, or phosphorylation, to contain negatively charged groups for adsorbing or attaching the compositions herein (e.g., positively charged arginine polymers). The artificial vessel segments can also be designed to be partially porous and to provide a reservoir region from which the compositions herein can gradually diffuse after it is grafted into a patient. While intimal hyperplasia, inflammation, restenosis or other vascular conditions cannot occur in artificial vessel segments, the invention herein contemplates the therapeutic effects that the composition can have on the anastomotic junctions where the artificial segments join the subject's vascular system. As used herein, the term "isolated" when referring to a graft or a conduit refers to that graft or conduit, as it exists outside the patient's body. For grafting, the vessel conduit may be of any suitable length. For example, a graft can be 1-20 inches long, more preferably 2-15 inches long, more preferably 3-10 inches long, or more preferably 4-8 inches long.

Thus, the present invention contemplates the application of NO enhancers, more preferable arginine polymers, or more preferably arginine homopolymers to isolated conduits ex vivo. It also contemplates the application of any of the above compositions in vivo to the conduit prior to, during, or post grafting. For example, a saphenous vein or an internal mammary artery can be contacted in situ prior to ablation with one or more of the compositions herein. After contact with the compositions, a segment of the vein is removed and grafted onto the heart. In another embodiment, a vein graft is contacted with the compositions herein ex vivo prior to grafting onto the heart.

It is preferable that the compositions herein be dissolved in sterile, physiologically suitable liquid that minimizes disruption of the physical and biological function of the vessel conduit. Exemplary liquids include serum-free culture media, (e.g., DMEM), aqueous saline NaCl solutions (e.g., 0.5-2.0% (w/v) saline or more preferably 0.7-1.0% (w/v) saline), any perfusion or organ preservation solution known in the art or disclosed herein, or any other sterile liquid medium or solution that is used in vessel grafting procedures.

Dosages and/or concentrations of a NO enhancers applied to a graft or target vein or artery may vary depending on, for example, the size of the graft and the NO enhancer used. Preferably, the graft is contacted with a solution comprising approximately between 0.001 µM-100 mM of a NO enhancer (s), more preferably from 0.01 µM-10 mM of a NO enhancer (s), more preferably from 0.1 µM-1 mM of a NO enhancer(s), and more preferably from 1 µM-500 µM of a NO enhancer(s), although concentration above or below these ranges may also be used. In some embodiments, a graft is contacted with 0.001 mg-10 g of a NO enhancer(s), more preferably 0.01 mg-5 g of a NO enhancer(s), more preferably 0.1 mg-1 g of a NO enhancer(s), or more preferably 1 mg-500 mg of a NO enhancer(s).

Generally, the conduit is contacted with the NO enhancer, more preferably arginine polymer, or more preferable arginine homopolymer for a time sufficient to allow for the NO enhancer to be translocated into the cells of the graft and reduce intimal hyperplasia, atherosclerosis, stenosis, or other vascular conditions occurring post-grafting. For example, the vessel is contacted with the compositions herein for about 0.1-24 hours, or more preferably 1-240 minutes, more preferably 10-60 minutes, or more preferably for a period of time less than 30 minutes. The conduit may be immersed in the solution, ex vivo, so that the compositions herein penetrate both the interior and exterior walls of the vessel. In the alternative, the compositions herein can be applied to the interior surface of the vessel and the vessel may be clamped or ligated at both ends such that only the intraluminal surface of the vessel is in contact with the compositions. In embodiments wherein the compositions are formulated as perfusate or preservation solutions, the vessels can be contacted with the compositions for longer periods of time (e.g., days). If the compositions herein are not formulated as perfusate or preservation solutions then lesser contact time is preferable. Generally, the contacting step can be performed at any appropriate temperature, but preferably at a temperature ranging from 0° C. to 40° C., more preferably 2° C. to 30° C., or more preferably 4° C. to 20° C.

The site where the vessel conduit is to be grafted can be prepared by conventional methods. Damaged or necrotic tissue is removed and the site is surgically prepared for attachment of the new vessel conduit, preferably during the time that the vessel conduit is being contacted with the compositions herein. Following the graft procedure, a patient may be monitored to verify physiological acceptance of the graft and to assess the levels of blood flow through the grafted vessel over time. It may appropriate to administer additional NO enhancer(s) to the conduit, the junctions of the conduit and the patient's vessels, or simply the patient's vessels surrounding the transplanted conduit after the transplant. Such compositions may be administered locally, e.g. by microinjection.

In a similar manner, the compositions herein can be used to treat vascular conditions associated with the formation of an arteriovenous (AV) shunt. An AV shunt is formed by connecting an artery to a vein. AV shunts are frequently used for hemodialysis, especially for kidney failure. Generally, there are two types of shunts: a "natural shunt" that connects an artery to a vein directly, and an "AV graft" (also referred to as an "AV shunt") that uses a small conduit or vessel to connect the artery to the vein. A surgical operation is necessary to form an AV shunt. In patients requiring kidney hemodialysis, a dialysis machine may be connected to the AV shunt. AV-shunt surgical procedures are extremely common procedures in the United States.

However, AV shunts often fail due to a flow limiting stenosis at the venous anastomosis caused by venous anastomotic intimal hyperplasia (VAIH). It is postulated that VAIH may be the result of repeated exposure to high pressure from the dialysis machine or the unopposed arterial pressure when not attached to the dialysis machine, which can lead to hyperplasia and stenosis within the vein. See Himmelfarb J., *Curr. Opin. Nephrol. Hypertens.* (1999) 8(5):569-72; Woods et al., *Nephrol. Dial. Transplant.* (1997) 12(4):657-9. Thus, the present invention contemplates the application of NO enhancers, more preferably arginine polymers, or more preferably arginine homopolymers to the AV graft, the venous anastomosis, and/or the arterial anastomosis, to prevent VAIH or other vascular conditions associated with the formation of the AV shunt.

In typical embodiments, an AV shunt is contacted with one or more of the compositions herein prior to, during, or post grafting. For example, the graft can be immersed in a solution containing one or more NO enhancers. Alternatively, the graft can be infused intraluminally with one or more NO enhancer and one or both ends of the graft can then be clamped or ligated such that only the intraluminal walls of the vessel are contacted.

The AV graft can be an autograft, allograft, or xenografts. The AV graft can vary in length as required. Preferably, an AV graft is about 1-15 inches long, more preferably about 2-10 inches long, and more preferably about 3-5 inches long. The NO enhancers herein can be formulated as a solution that can be applied directly to the graft. Such a solution can have a concentration ranging from 0.001 µM-100 mM, more preferably from 0.01 µM-10 mM, more preferably from 0.1 µM-1 mM, and more preferably from 1 µM-500 µM of a NO enhancer herein, although concentration above or below these ranges can also be used. In other embodiments, a graft is contacted with 0.001 mg to 10 g of a NO enhancer, more preferably 0.01 mg to 5 g of a NO enhancer, more preferably 0.1 mg to 1 g of a NO enhancer, or more preferably 1 mg to 500 mg of a NO enhancer.

In preferred embodiments, the AV graft is contacted with the compositions herein for less than 24 hours, more preferably less than 240 minutes, more preferably less than 60 minutes, or more preferably less than 30 minutes. However, in embodiments wherein the compositions are formulated as perfusate or preservation solutions, the vessels can be contacted with the compositions for longer periods of time (e.g., days). If the compositions herein are not formulated as perfusate or preservation solutions then lesser contact time is preferable. Generally, the contacting step can be performed at any appropriate temperature, but preferably at a temperature ranging from 0° C. to 40° C., more preferably 2° C. to 30° C., or more preferably 4° C. to 20° C.

The NO enhancers herein can also be used to treat peripheral arterial disease (PAD). PAD refers to damage to the peripheral arteries, which is caused by arterial hypertension and/or formation of plaques. Generally, where the arteries are blocked by cholesterol deposits the PAD condition is also known as atherosclerosis, and where the arteries are blocked by mineral deposits, the condition is known as arteriosclerosis.

PAD is a common disorder that occurs when an artery segment, which normally has smooth lining, becomes narrow and rough allowing clots to form on the walls, thus further narrowing the artery. As a result of the arteries narrowing, organs (e.g., brain, heart, legs, kidney) receive inadequate amounts of blood. This can result in cramping of the organs and/or muscles surrounding the organs. However, some people, especially those suffering from type-1 diabetes, do not experience any pain or symptoms from PAD. This may be referred to as "silent PAD."

PAD is often diagnosed using any one of the following means: medical history and physical examination, ankle-brachial index (ABI), treadmill exercise test, reactive hyperemia test, segmental pressure measurements, PVR waveform analysis, duplex arterial imaging or ultrasound imaging, photoplethysmography, and arteriogram. Once diagnosed, PAD is often treated by life style changes (quit smoking), exercise, drugs (e.g., Clopidogrel, cilostazol, aspirin and cholesterol lowering drugs), or surgery. Surgery can involve endarterectomy, which is the opening of the artery, cleaning it, and suturing it back together. Endarterectomy works best for pelvis (iliac arteries) or groin (femoral arteries) blockage. Other blockages may be bypassed using a bypass surgery. Bypass surgeries to treat PAD include, but are not limited to, aortobifemoral (wherein blood routed from the abdominal aortic artery to both femoral arteries), femoropopliteal (wherein blood routed from the femoral to the popliteal artery), and femorotibial (wherein blood routed from the femoral to a tibial artery).

For smaller arteries, angioplasty or stenting may be more effective. Angioplasty is widely used for treatment coronary and peripheral arterial disease due to blockage. This procedure is relatively simple and requires only a small incision in the groin to introduce the instrument. The instrument is passed through the vessels until it reaches to target region. A balloon at the tip of the instrument is then inflated to compress the plaque and enlarge the artery, thus providing an area for blood to flow through. Thus, the compositions herein can be used in an angioplasty procedure to coat the balloon and/or, potentially, follow-up with localized delivery to the target vessel. Various forms of drug delivery balloons are described in WO92/11895, WO95/05866 and WO96/08286, which are incorporated herein by reference for all purposes.

In many cases, stenting is preferable to angioplasty. Stents are scaffolds that can be inserted into an artery either prior to, during, or post angioplasty procedure, or as an alternative to an angioplasty procedure. The present invention contemplates the use of a stent for opening of an artery or a vein in conjunction with the administering of NO enhancers, preferably arginine polymers, or more preferably arginine homopolymers to the stent area. In preferred embodiments, the NO enhancers are administered locally. Local administration can be accomplished by any means known in the art, including preferably, the use of a Dispatch™ catheter, such as the one made by Sci Med, Maple Grove, Minn. The NO enhancers can be administered in vivo and locally prior to, during, or post stenting or angioplasty.

The NO enhancer can be administered independently or in combination with one or more additional agents. Additional agents that may be administered include, but are not limited to, paclitaxel, ascomycin, etc.

Recently, the development of coated stents, also known as drug-eluting stents, has allowed for the stent to be coated or imbedded with timed-release drugs that can prevent restenosis. Thus, the present invention contemplates the use of the compositions herein with drug eluting stents to prevent restenosis. In one embodiment, the present invention contemplates the use of one or more NO enhancers, preferably arginine polymers, or more preferably arginine homopolymers to coat a stent. Preferably, the NO enhancer composition is formulated for slow release. The NO enhancer composition may be imbedded within the stent either independently or in combination with one or more additional therapeutic agents. Effective dosages may widely vary; any dosage that restores circulation through a stenosed or restenosed blood vessel and/or alleviates the narrowing of the affected area is acceptable for use in the invention.

The manner by which the effective compounds are bonded to the stent can also provide either slow or fast release of the effective compounds. Slow release of the effective compound can take up to ten years. Preferably, the release period that allows for the compositions herein to be released from the stent or delivery device into the circulation to alleviate narrowing effect. Application of the compositions herein to a stent or other local-delivery device can be achieved in a number of different ways.

First, the compound can be mechanically or electromechanically bonded to the delivery device, e.g. by a covalent bonding process. When using such a physical application the compounds are directly embedded into a metal or other suitable substance from which the local-delivery system is comprised.

Second, the effective composition can also be applied using a chemical coating/bonding process, whereby layers of a suitable pharmaceutical agent, vehicle, or carrier entrap the compound. In this manner, a biological or pharmacological coating already present on the local-delivery device acts as a platform for coating the compounds described above. Examples of platforms include, but are not limited to, silicon carbide, carbon, diamond or diamond-like coating, e.g. polytetrafluoroethylene, hylauronic acid or polyactone. Other suitable synthetic pharmaceutical agents include, but are not limited to, phosphorylcholine, polyurethane, segmented polyurethane, poly-L-lactic acid, cellulose ester, polyethylene glycol as well as polyphosphate esters. Naturally occurring vehicles or carriers include collagens, laminens, heparins, fibrins, and other naturally occurring substances that absorb to cellulose. Using a chemical coating of the stent or other device is particularly advantageous in that it allows the compounds to slowly release from the carrier, vehicle, or agent. This extends the time that the affected portion of the body sustains the efficacious effects of the compounds. The manner in which these carriers or vehicles interact with the device material as well as the inherent structure of these carriers and vehicles provide a diffusion barrier, thereby controlling the release of the entrapped compounds. In other words, the manner by which the effective compounds are chemically bonded to the stent or delivery device can control slow or fast delivery of the compound.

In addition to NO enhancers, additional therapeutic agents may be coated or imbedded in the stent. Such agents include paclitaxel, ascomycin, etc.

The compositions herein can also be used to treat renal vascular conditions such as malignant nephroangiosclerosis, infarction from occlusion of major renal vessels, sclerodermna, atheromatous embolization, renal cortical necrosis, renal vein thrombosis, necrotizing arteritis, and Wegener's granulomatosis.

Malignant nephroangiosclerosis appears in most cases as accelerated cardiovascular disease in the course of idiopathic hypertension, especially in untreated cases. Thus, approximately 20% of patients having this condition may also experience renovascular hypertension. Most malignant nephroangiosclerosis cases occur in men during their 40's and 50's. Malignant nephroangiosclerosis is characterized by fibrinoid necrosis of arterioles. In particular, interlobular arteries show a considerable amount of intimal thickening by a fine concentric layering of collagen, which may cause a complete obliteration of the vascular lumen. Patients suffering from malignant nephroangiosclerosis are often kept alive by kidney dialysis and are often administered anticoagulants.

Renal infraction is a localized area of ischemic necrosis caused by either renal arterial or venous occlusion, which is usually caused by embolism, arteriosclerotic narrowing, or trauma. Common treatments involve oercutaneous tranluminal angioplasty or fibrinolytic therapy. Anticoagulants are also administered to many patients.

Atheroembolic renal disease is a condition involving the deterioration of renal function as caused by atheromatous material obstructing the renal artery. This condition can occur spontaneously or subsequent to vascular surgery or arteriography. Patients suffering from this condition are often hypertensive and may experience widespread peripheral embolism, however there is no diagnosis for this conditions except for by renal biopsy. Furthermore, there are no known treatments currently available for this condition.

Renal cortical necrosis is a rare form of arterial infraction characterized by necrosis of cortical tissues with sparing of the medula. Predisposition to this condition involves nephrotoxins, renal ischemia, intravascular coagulation, and hyperacute renal allograft rejection. Patients suffering from renal cortical necrosis are generally treated with kidney dialysis.

Renal vein thrombosis occurs with hypercoagulability. In acute cases, these conditions can be diagnosed using an ultrasonography to detect an enlarged kidney. Furthermore, if a contrast agent is administered the ultrasonography shows that no excretion is made. Common treatment includes anticoagulant therapy, thrombolytic therapy with streptokinase or urokinase, and less frequently nephrectomy or surgery is used.

Thus, the present invention contemplates the use of the compositions herein to treat or prevent renal vascular conditions. For example, one or more NO enhancers, more preferably an arginine polymer, or more preferably an arginine homopolymer can be administered in vivo to kidney tissue.

The present invention also contemplates the use of the compositions herein to treat or prevent pulmonary vascular conditions. Such conditions include, but are not limited to, atelectasis, acidosis, acute bronchitis, acute mountain sickness, acute pulmonary edema, acute pulmonary thromboembolism, adult respiratory distress syndrome, bronchial asthma, emphysema, fat embolism in the lung, heparin protamine reactions, hypertension, hypoxia, hyaline membrane disease, inflammation of the lung, Kartaagener's syndrome, Legionnaire's disease, panacinar emphysema, persistent pulmonary hypertension of newborn, post cardiac surgery acute pulmonary pneumonia, prenatal aspiration syndrome, pulmonary arterial hypertension, and chronic obstructive pulmonary disease.

Pulmonary arterial hypertension (PAH) and chromic obstructive pulmonary disease (COPD) are common pulmonary vascular conditions associated with vasoconstriction. PAH refers to a group of diseases characterized by a rise in pressure in the pulmonary artery (the blood vessel that leads from the heart to the lungs) above normal levels. PAH is a severe disease that can become life threatening if undetected or untreated. PAH can be etiologically divided into two forms: primary pulmonary hypertension (PPH) refers to pulmonary hypertension occurring in the absence of a known cause and secondary pulmonary hypertension (SPH) refers to PAH occurring from a known cause.

It is estimated that 1 to 2 individuals per one million suffer from PPH. While PPH affects both genders equally during childhood, after puberty PPH is more prevalent in women than in men. Currently, about a quarter of all patients suffering from PPH are treated with calcium channel-blocking drugs that are administered orally. Those who do not respond to the calcium channel-blockers are placed on continuous intravenous infusion of prostacyclin (a vasodilator). Anticoagulants, diuretics and supplemental oxygen are also used for treatment.

SPH is more common that PPH though largely underdiagnosed. The most common causes for SPH include emphysema and bronchitis. Other causes for SPH include scleroderma, CREST syndrome, and systemic lupus erythematosus. SPH can also be caused by congenital heart diseases, chronic pulmonary thromboembolism, HIV infection, liver disease, and diet drugs. Treatment of SPH includes correction of the underlying cause and reversal of hypoxemia. Further more, lung transplantation remains an option for selected patients with pulmonary hypertension that does not respond to medical management. See *Am. Fam. Physician*, (2001) 63:1789-98, 1800.

COPD is an umbrella name for several lung diseases including asthmatic bronchitis, chronic bronchitis (with normal airflow), chronic obstructive bronchitis, bullous disease, and emphysema. COPD was the fourth leading cause of death in the United States in 1998, accounting for over 10,000 deaths.

The primary cause for COPD is smoking. Other causes for COPD include an inherited deficiency in an enzyme known as alpha-1-antitrypsin deficiency, industrial pollutants, aerosol sprays, non-tobacco smoke, internal-combustion engine exhaust, and physiological atrophy associated with old age (senile emphysema). COPD conditions develop from damage to the alveoli and the bronchioles, leading to their collapse. When the alveoli collapse, some oxygen stays in the lung and becomes "stale." Other parts of the lung must substitute for the collapsed alveoli, leading to over-inflation, inflammation of the lungs, and a feeling of shortness of breath.

The most important treatment of COPD is the cession of smoking. Other drug treatments include fast-acting beta-2-agonists (e.g., albuterol) and anticholinergic bronchodilators (e.g., ipratropium bromide and theophylline derivatives) to open airways. In addition, long-acting bronchodilators can also be used to relieve constriction of airways and prevent bronchospasm associated with COPD. Inhaled or oral corticosteroids may be administered to help reduce inflammation. Antibiotics may be administered to prevent further damage by infection. Expectorants may be administered to help loosen and expel mucus secretions from the airways. Diuretics may be administered to reduce access water retention associated with right-heart failure that occurs in some COPD patients. Digitalis (usually in the form of digoxin) may be administered to strengthen the force of the heartbeat. Other treatments including painkillers, cough suppressants, and sleeping pills, may be administered to depress breathing.

Thus the current invention contemplates the use of NO enhancers, more preferably arginine polymers, and more preferably arginine homopolymers in the treatment and/or prevention of pulmonary vascular conditions, including PAH and COPD. In preferred embodiments, the NO enhancers are formulated as aerosols or solutions for direct administration (e.g., via inhalation or via a bronchoscope) to the alveoli and bronchioles. The NO enhancers can be administered independently or co-administered with one or more additional therapeutic agents disclosed herein (e.g., corticosteroids, antibiotics, expectorants, diuretics, digitalis, etc.).

It is also contemplated by the present invention that vascular conditions associated with sexual dysfunction may be treated and/or prevented with the compositions herein. Vascular conditions associated with sexual dysfunction include, but are not limited to, erectile dysfunction, Peyronie's syndrome, priapism, premature ejaculation, female sexual dysfunction, vaginal lubrication, vaginal engorgement, pain during intercourse (e.g., dyspareunia or vulvadynia), preeclampsia, urologenital infections, vulvodynia and estrogen depletion conditions such as menopause, post-menopause, and hot flashes.

In one example, the present invention contemplates the use of the compositions herein for the treatment of erectile dysfunction. Erectile dysfunction is a vascular condition whose symptoms include the total inability to achieve erection, an inconsistent ability to do so, and a tendency to sustain only brief erections. It is estimated that 15-30 million Americans suffer from erectile dysfunction. While the incidence of erectile dysfunction increases with age (about 5% of 40-year-old men and 15-25% of 65-year-old men experience erectile dysfunction), erectile dysfunction is usually caused by disease, injury, or side effects from other drugs and not age.

Treatment for erectile dysfunction varies from least invasive, psychotherapy, to most invasive, surgery. However, most erectile dysfunction cases are treated using drugs that can be taken orally, injected directly into the penis, or inserted into the urethra at the tip of the penis. An alternative treatment provides a mechanical vacuum device that can be used to cause an erection by creating a partial vacuum, which draws blood into the penis, engorging and expanding it.

The current invention contemplates the use of NO enhancers for the treatment and/or of sexual dysfunction vascular conditions, including erectile dysfunction. Thus a patient suffering from erectile dysfunction may be administered an NO enhancer, more preferably an arginine polymer, and more preferably an arginine homopolymer. Preferably, the NO enhancer is administered locally, e.g. by topical application or subcutaneous application. For topical application, the NO enhancer may be formulated as a gel or as a solution that can be applied locally to the penile arterial blood vessel and/or the trabecular meshwork. For subcutaneous administration the NO enhancer may be formulated as a solid, solution, or gel. The NO enhancer can be administered independently or co-administered with additional therapeutic agents that increase blood flow into the cavernous bodies of the penis.

In another example, the present invention contemplates the use of the compositions herein for the treatment of vulvodynia. Vulvodynia (also known as vulvar dysesthesia) is characterized by itching, burning, stinging or stabbing sensations in the area around the opening of the vagina. Symptoms of vulvodynia may range from mildly irritating to completely disabling. While a distinct sore or area of redness may be visible, often the vagina shows no abnormalities or infections on gynecological and/or dermatological evaluations. It is estimated that five percent of all women will experience vulvodynia before the age 25. However, until recently, there have been no drug treatments for vulvodynia. Instead, patients diagnosed with this condition are prescribed dietary changes, vitamin supplements, muscle relaxants, biofeedback therapy, electrical stimulation, and psychotherapy. See Newman, *Ostomy. Wound. Manage.* (2000) 46(12):48-54.

Recently, it has been suggested that vulvodynia is caused by abnormality in the muscles of the pelvic floor. See Glazer H I, *J. Reprod. Med.* (2000) 45(10):798-802. As a result, some are experimenting with treatment using botulinum toxin (botox) injections. Botox is a toxin, which causes muscle paralysis when injected. In women suffering from vulvodynia, botox may be injected into pelvic walls to reduce muscle contractions and/or muscle pain.

The present invention contemplates the use of NO enhancers, more preferably arginine polymers, and more preferably arginine homopolymers for the treatment and/or prevention of vulvodynia. Preferably, NO enhancers (e.g., poly-L-arginine and R9) are formulated for localized application. For example, a NO enhancer can be formulated into a gel or an ointment and applied vaginally to the pelvic walls.

In one example, a NO enhancer is formulated as a solid suppository or a gel and administered vaginally or subcutaneously. Preferably, the NO enhancer is formulated for slow release. Formulations of the compositions herein may be admixed with additional therapeutic agents such as muscle-relaxers or painkillers. Alternatively, a treatment regimen may include separate applications of NO enhancers and additional therapeutic agents.

Ocular vascular conditions that can be treated and/or prevented with the compositions herein include, but are not limited to, cataract, intraocular pressure, dry eye, diabetic retinopathy, and glaucoma. Glaucoma is an ocular vascular conditions associated with vasoconstriction causing a particular pattern of optic nerve damage. While this pattern of damage usually occurs as a result of increased intraocular pressure, it may also occur with normal or even below-normal ocular pressure.

Worldwide, it is estimated that about 50 million people suffer from glaucoma. In the United States, there are more than three million people diagnosed with glaucoma and about 300,000 new cases are diagnosed each year. Glaucoma's effects can range from mild vision impairment to complete blindness. Unfortunately, many of those affected by glaucoma may not be aware of the disease as its early stage symptoms may not be easily apparent. By the time a patient exhibits ocular conditions associated with the disease, considerable damage has already occurred. Medications and surgery can help slow down the progression of glaucoma but they cannot cure vision lost.

Glaucoma is generally divided into two forms: primary and secondary. There are two types of primary glaucoma: (1) chronic open-angle and (2) acute or chronic angle-closure glaucoma. Chronic open angle glaucoma (COAG) is the most prevalent form of glaucoma and accounts for nearly 85% of all cases. COAG is caused by malfunctioning of the drainage system between the anterior and posterior chambers of the eye. In a healthy eye, aqueous humor is formed in the posterior chamber of the eye by the ciliary body and processes at a rate of approximately 2.5 microliters per minute. The humor then passes around the lens, through the papillary opening in the iris, and into the anterior chamber of the eye. The aqueous humor drains out of the eye via either a "uveoseleral" route or a "canalicular" route. The uveoscleral route involves drainage between the muscle fibers of the ciliary body and accounts for approximately 15-20% of aqueous drainage. The canalicular route involves drainage thought the trabecular meshwork into the Schlemm's canal. The production of humor in a healthy eye is equal to aqueous outflow and intraocular pressure remains fairly constant in the range of 10 to 20 mmHg.

In COAG, there is an abnormal resistance along the outer aspect of the trabecular meshwork and the inner wall of the Schlemm's canal. It is believed that this resistance is a result of abnormal metabolism of the trabecular cells leading to an excessive buildup of extracellular material or a buildup of abnormally "stiff" materials in this region. As fluid builds up due to reduced drainage of aqueous humor, the pressure inside the eye, referred to herein as intraocular pressure (IOP) rises. Unless IOP is controlled, the increased pressure can lead to damage the optic nerve, resulting in progressive visual loss and even blindness.

Agents that have been suggested in the topical treatment of COAG include pilocarpine, timolol maleate, betataxolol HCl, epinephrine, dipivefrin, demecarium bromide, echothiophate iodide. See Merck Manual, (15$^{th}$ Ed. Merck Sharp & Dohme Research Labs. 1987). Systemic agents administered to treat COAG include carbonic anydrase inhibitors. Other agents have also been suggested to the treatment of COAG. See EP 257887 (alkaloids); EP 291999A2 (atrial natriuretic factor peptides); U.S. Pat. No. 4,722,933 (substituted 2-aminotetralins); U.S. Pat. No. 4,515,800 (phenylimino-imidazoles); U.S. Pat. No. 4,694,022 (betaxolol salts); U.S. Publication Application No. 2002/0168424 (NO donors such as minoxidil, nitroglycerin, monomeric L-arginine, isosorbide dinitrate and nitroprusside in combination with a cyclic guanosine 3',5'-monophosphate specific phosphodiesterase type 5 (cGMP-PDE5) inhibitor); U.S. Publication Application No. 2003/0153626 (A3 subtype adenosine receptor antagonists, calmodulin antagonists and antiestrogens); U.S. Publication Application No. 2003/0153613 (potassium channel blockers); U.S. Publication Application No. 2003/0153501 (oncomodulin and a cAMP modulator); and U.S. Publication Application No. 2003/0060511 (15-keto-prostaglandin compound).

Acute angle-closure glaucoma (AACG) and chronic-angle-closure glaucoma (CACG) are characterized by attacks of sudden increased IOP, usually unilateral, with severe pain and loss of vision, caused by acute obstruction of acquires drainage with the eye. Such conditions are treated with compositions used to treat COAG. Secondary glaucoma, on the other hand, is a condition caused by other disorders or conditions such as intraocular tumors, intumescent cataracts, central retinal vein occlusion, trauma to the eye, operative procedures, inflammatory disease, and intraocular hemorrhage, which result in complete posterior synechia and iris bombe. Treatment of secondary glaucoma usually involves treating the underlying cause.

The current invention contemplates the use of NO enhancers, more preferably arginine polymers, and more preferably arginine homopolymers for the treatment and/or prevention of vascular ocular conditions including glaucoma. Preferably, a poly-L-arginine or an R9 composition is administered directly to the target tissue (e.g., outer aspect of the trabecular meshwork or inner walls of the Schlemm's canal). Direct administration can be accomplished, for example, by topical application or by localized microinjections. The NO enhancers can be administered independently or co-administered with one or more additional therapeutic agents disclosed herein.

It is also contemplated that the compositions herein may be used to treat dermal vascular conditions including, but are not limited to, skin aging, necrotizing fascitis, decubitus ulcers, anal fissures, Raynaud's phenomenon, scleroderma, hair loss (e.g., Alopecia Areata, hair loss in patches believed to be an immunologic disorders Alopecia Totalis, hair loss over the entire scalp, Alopecia Universalis, loss of all hair, all over the body, Anagen Effluvium, sudden loss of growing hairs which is often caused by chemotherapy, Telogen Effluvium, sudden hair loss when large numbers of follicles enter the resting phase which is usually temporary and may be caused by severe stress, medications, etc.), diffused cutaneous systemic sclerosis, frostbites, and wound healing.

Wound healing involves the repair and reconstruction of tissue, e.g.; skin, muscle, neurological tissue, bone, soft tissue, internal organs, and vascular tissue. Wounds are generally categorized into four stages. Stage I wounds are characterized by redness or discoloration, warmth, and swelling or hardness. Stage II wounds partially penetrate the skin. Stage III wounds describe full-thickness wounds that do not penetrate the tough white membrane (fascia) separating the skin and fat from the deeper tissues. Stage IV wounds involve damage to muscle or bone and undermining of adjacent tissue. Stage IV wounds may also involve the sinus tracts (red streaks indicating infected lymph vessels).

Wounds can result from either acute or chronic injury. Chronic wounds are a frequent problem for elderly and bedfast patients. An ulcer or a wound is an open sore on the skin (or a mucous membrane) that causes destruction of the surface tissue. An ulcer can be shallow or deep and is usually inflamed and painful. There are numerous types of ulcers including, for example, traumatic ulcers, arterial ulcers, venous ulcers, diabetic foot ulcers, and pressure ulcers. Burns are another form of wounds.

Generally, wounds heal in the following three stages: inflammation, proliferation and maturation. The inflammation stage occurs in the initial days following an injury. During inflammation, the wound area attempts to restore homeostasis by constricting blood vessels to control bleeding, releasing platelets and thromboplastin to generate a clot, and releasing cytokines to generate an inflammatory response. Next, in the proliferation stage, granulation occurs. Granulation involves epithelialization (growth of new skin), angiogenesis (blood vessel regeneration), and generation of new collagen by fibroblast cells. Granulation can last 3 weeks or longer depending on the severity of the wound. Finally, in the maturation stage, new collagen forms, changing the shape of the wound and increasing strength of tissue in the area. This often forms a scar. The maturation stage can last for up to 2 years.

Wound healing generally does not respond to conventional treatments that are used to treat superficial cuts. Currently, there are no specific treatments to wound healing aside from keeping the area moist and providing to the area nutrients, including angiostatic steroids, sex steroids, bromelain, vitamin B-complex, vitamins A, E and C, zinc, chondroitin insulfate, copper, ornithine alpha-ketoglutarate (OKG), arginine monomers, carnosine, and glucosamine sulfate.

Thus, the present invention contemplates the use of NO enhancers, preferably arginine polymers, and more preferably arginine homopolymers, for the treatment and enhancement of wound healing. Preferable the NO enhancers are administered topically to the wound region. Formulations for topical administration are disclosed herein. The number of applications per treatment cycle may vary according to the severity of the wound and may be determined by a physician. The NO enhancers can be administered independently or co-administered with additional therapeutic agents or nutrients (e.g. steroids, vitamins, minerals and trovafloxacin).

Similar to wound healing, the present invention also contemplates the use of NO enhancer(s) for the treatment of frostbites. Frostbite is an injury caused by exposure to cold temperatures, which does not necessarily need to be below freezing. The cold temperature causes ice crystals and clots to form and can result in poor perfusion to the face and the extremities, leading to dehydration and cell death. If the exposure continues, damage may occur to underlying blood vessels, nerves, and muscles.

When patients receive medical care quickly, frostbite is often reversible because the injury is less severe. If treatment is delayed, patients may have long-term medical problems. The NO enhancers herein can be helpful in the reperfusion of vessels injured by frostbites. Thus, the present invention contemplates the use of NO enhancers, preferably arginine polymers, and more preferably arginine homopolymers, for the treatment of frostbites. The NO enhancer(s) are preferably formulated for localized administration (e.g., topical administration of a gel or a solution). The compositions herein can further include additional therapeutic agents, such as, for example, reserpine, pit viper venom, phenoxybenzamine, heparin, and dextran. Other forms of reperfusion injury follow cerebral vascular accidents or myocardial infarction and may be amenable to treatment with NO enhancers in a similar manner. Thus, the present invention contemplates the use of NO enhancers for the prevention and/or treatment of instances where blood flow begins anew to hypoxic tissues.

In another embodiment the present invention contemplates the use of the compositions herein for the treatment of anal fissures. Anal fissures are breaks in the skin that lines the anal canal. While mild cases of anal fissures involve only superficial tear in the tissue that lines the anal canal, these tears can deepen and reach underlying tissue of the internal sphincter. Anal fissures occur mostly in young people, and generally as a result of passage of a hard stool that traumatizes the anus. Most patients who develop anal fissures have a higher than normal pressure in the anal canal. In a small percentage of cases, anal fissures stem from other causes, such as Crohn's disease or certain infections. Currently, treatment of anal fissures includes sitz baths, suppositories or stool bulking agents to treat constipation, and topical nitroglycerin ointment to alleviate pain. It has been suggested that compounds that release NO, such as nitroglycerin, ethylene glycol dinitrate, glyceryl 1,2-dinitrate, glyceryl, 1,3-dinitrate, glyceryl 1-mononitrate, butane 1,2,4-triol-triinitrate, mannitol hexanitrate, pentaerythrityl tetranitrate, pentaerythrityl trinitrate, isosorbide dinitrate, isosorbide mononitrate, and erythrityl tetranitrate may be used for the treatment of anal fissures. See U.S. Pat. No. 5,504,117 (incorporated herein by reference for all purposes). However, severe anal fissures may require surgical therapy as an alternative or in addition to drug treatment. Recently, anal fissures have been treated with botox injected into the anal sphincter to lower the pressure and allow the fissures to heal.

The present invention contemplates the use of NO enhancers, more preferably arginine polymers, and more preferably arginine homopolymers for the treatment and/or prevention of anal canal disorders including anal fissures. In particular, the present invention contemplates a pharmaceutical composition comprising an active ingredient arginine homopolymer, e.g. R9, for the treatment/prevention of anal fissures, anal ulcers, and levator spasm. In some embodiments, the pharmaceutical compositions are formulated for topical administration. In other embodiments, the pharmaceutical compositions are formulated for subcutaneous administration (e.g., via a microinjection).

The compositions may be co-administered with additional therapeutic agents, including, for example, painkillers, antibacterial, antifungal, and anti-inflammatories. In one example, a suppository of both a R9 polymer and an anesthetic composition is formulated into a gel, cream or solution and administered rectally to a patient suffering from anal fissures.

The invention herein also contemplates the local administration of compositions that increase the metabolic production of NO for the treatment of Raynaud's phenomenon. Raynaud's phenomenon is a condition in which circulation of blood to the extremities is interrupted. This usually occurs as a result of touching cold objects, exposure to cold, emotions, and smoking. However, people who work with vibratory tools are also prone to Raynaud's phenomenon, Raynaud's can range in severity from minor discomfort to the onset of ulcers or even gangrene. Raynaud's often starts at young age and progresses slowly over thirty years or more. Primary Raynaud's occurs spontaneously without an underlying condition being present. Raynaud's affects women nearly ten times more than men. There is some suggestion that primary Raynaud's is hereditary. Secondary Raynaud's is less common than the primary Raynaud's and is associated with an underlying disease, e.g., scleroderma, systemic lupus erythematosus, Sjögrens syndrome and rheumatoid arthritis. This is more serious and early and accurate diagnosis is essential.

Scleroderma, another dermal vascular condition, is symptomatic when either external skin or an internal organ becomes stiff, tight, and shiny due to swelling or thickening of the connective tissue. Approximately 300,000 individuals in the United States have scleroderma. Scleroderma, like Raynaud's phenomenon, is more common in women than in men. Internal organs that are commonly affected by scleroderma include the esophagus, gastrointestinal tract, lungs, kidneys, and heart. Scleroderma may also affect blood vessels, muscles and joints. Currently, there are no known treatments for scleroderma.

According to the present invention, NO enhancers, more preferably arginine polymers, and more preferably arginine homopolymers, are used to treat and/or prevent dermal vascular conditions including Raynaud's and scleroderma. Preferably, the NO enhancers are administered topically or subcutaneously to the affected areas. For topical administration, the NO enhancers are formulated as gels, ointments, creams, and lotions. For subcutaneous administration, the NO enhancers are formulated as solutions or gels. For example, a patient suffering from Raynaud's or scleroderma may be administered a therapeutically effective amount of a NO enhancer (e.g., R9 or a poly-L-arginine) by topically applying a solution or gel comprising the NO enhancer. The NO enhancers can be administered independently or in combination with one or more therapeutic agents, e.g., a painkiller or a corticosteroid.

III. Formulations and Use

The compositions herein may be formulated into pharmaceutically acceptable salts and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cycloexylsulfonate, cyclohexylsulfamate, and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Pharmaceutical compositions can be formulated from active compositions and/or salts thereof by standard techniques using one or more suitable carriers, excipients, and diluents. See, e.g., Remington's Pharmaceutical Sciences, (19th Ed. Williams & Wilkins, 1995) (incorporated herein by reference for all purposes).

Examples of suitable carriers, excipients and diluents include lactose, dextrose, sucrose, sorbitol, mannitol, starches, gum acacia, calcium phosphate, alginates, calcium silicate, microcrystalline cellulose, polyvinyl pyrrolidine, cellulose, tragacanth, gelatin syrup, methylcellulose, methyl and propyl hydroxybenzoates, talc, magnesium stearate, water and mineral oil. Other additives optionally include lubricating agents, wetting agents, emulsifying and suspending agents or preserving agents. An ophthalmic carrier is preferable in sterile, substantially isotonic aqueous solutions. Such solutions will typically maintain sterility by employing well-known ophthalmic preservatives. The amount of these preservatives employed is generally about 0.001 to 0.1% by weight. Particularly suitable preservatives for ointments include methyl and propyl parabens.

The pharmaceutical compositions may be formulated to provide immediate, sustained or delayed release of the compound. For applications providing slow release, certain carriers may be particularly preferred. Suitable slow release carriers may be formulated from dextrose, dextran, polylactic acid, and various cellulose derivatives, for example ethylhydroxycellulose in the form of microcapsules.

Various additives may be added to the formulations herein. Such additives include substances that serve for emulsification, preservation, wetting, improving consistency and so forth and which are conventionally employed in pharmaceutical preparations. Other additives include compounds that have surfactant properties, either ionic or non-ionic such as sorbitan monolaurate triethanolamine oleate, polyoxyethylenesorbitan monopalmitate, dioctyl sodium sulfosuccinate, monothioglycerol, thiosorbitol, ethylenediamine tetra-acetic acid, etc.

Suitable preservatives for use in the pharmaceutical preparations include benzalkonium chloride, benzethonium, phenylethyl alcohol, chlorobutanol, thimerosal and the like. Suitable buffers include boric acid, sodium and potassium bicarbonate, sodium and potassium borates, sodium and potassium carbonate, sodium acetate, sodium biphosphate, Tris, and the like, in amounts sufficient to maintain the pH between about pH 3 and about pH 9.5, most preferably between about pH 7 and pH 7.5. Suitable tonicity agents are dextran 40, dextran 70, dextrose, glycerin, potassium chloride, propylene glycol, sodium chloride and the like, such that the sodium chloride equivalent of the ophthalmic solution is in the range of 9.9.+−.0.2%.

Suitable antioxidant and stabilizers include sodium and potassium bisulfite, sodium and potassium metabisulfite, sodium thiosulfate, thiourea and the like. Suitable wetting and clarifying agents include polysorbate 80, polysorbate 20, poloxamer 282 and tyloxapol. Suitable viscosity increasing agents include dextran 40, gelatin, glycerin, hydroxyethyl cellulose, hydroxymethyl propyl cellulose, lanolin, methylcellulose, petrolatum, polyethylene glycol, polyvinyl alcohol, polyvinyl polyvinylpyrrolidone, carboxymethyl cellulose and the like. Stabilizers such as chelating agents that may be used include, for example, EDTA, EGTA, DTPA, DOTA, ethylene diamine, bipyridine, 1,10-phenanthrolene, crown ethers, aza crown, catechols, dimercaprot, D-penicillamine and deferoxamine. Antioxidants that may also act as stabilizers include such compounds as ascorbic acid, sodium bisulfite, ascorbyl palmitate, butylated hydroxyanisole, butylated hydroxytoluene, potassium metabisulfite and sodium metabisulfite.

Antibacterial, antiviral, antifungal and anti-tumor agents may also be used in the pharmaceutical compositions herein. Such agents and their formulations are well known to those skilled in the art.

Viscosity agents are often added to prevent extensive drug loss by drainage once an aqueous preparation is instilled in the eye. Several compounds are suitable for this purpose, including methylcellulose, hydroxypropylmethylcellulose, polyvinyl alcohol, dextran, and hydroxyethylcellulose (Ludwig and Van Ooteghem, 1989).

The pharmaceutical compositions can be administered orally, parenterally by inhalation, topically, rectally, ocularly, nasally, buccally, vaginally, sublingually, transbuccally, liposomally, via an implanted reservoir (e.g., patch or stent) or via local delivery (e.g., by catheter). The term "parenteral" as used herein includes subcutaneous, intracutaneous, intravenous, intramuscular, intra-articular, intra-adipose, intra-arterial, intrasynovial, intrasternal, intrathecal, intra-vagina, intra-rectal, intralesional, intra-ocular, and intracranial injection or infusion techniques. Preferably, the pharmaceutical compositions are administered locally to effected area or tissue.

Ointment may be formulated with cetyl ester waxes, oleic acid, paraffin, petrolatum, hydrophilic petrolatum or white petrolatum. Other ointment components may include mineral oil, lanolin, anhydrous lanolin, glycerol monosteate or cetyl alcohol. Water-soluble ointment bases and components may incorporate glycol ethers and their derivatives, polyethylene glycols, polyoxyl 40 stearate and polysorbates.

Solid inserts for localized delivery (e.g., to the eye, vagina, rectum and penis) may also be employed. Such inserts will be in suitable form for the target area to be inserted. For example, an ocular insert may be in suitable form to be inserted into an area of the eye known as the cul de sac (a pocket-like area formed with the conjunctiva). Such an insert may include one or more active ingredients and may be biodegradable or non-biodegradable. In administering solids into the eye area, consideration should be given in the choice of biodegradable material as it may be affected by tears and lacrimal fluids. Inserts into the rectum and vagina may be in the form of a suppository or retention enemas. Such inserts may contain conventions suppository bases such as cocoa butter or other glycerides. Inserts into the urethra may be in the form of a tablet, suppository or other pill that may include biodegradeable and/or nonbiodegradeable materials.

Pharmaceutical compositions may also be formulated for depot preparations or slow release preparations. Such preparations can be administered by implementation (e.g., subcutaneously, intravaginally, intraocularly, intradermally, or intramuscularly) or by localized injections (e.g., subcutaneous).

Liposomal preparations are also contemplated by the present invention. One could incorporate the pharmaceutical compositions herein into various liposomes by mixing with the appropriate lipids or phospholipids.

The pharmaceutical compositions may be delivered using drug delivery systems. Such delivery systems include hyaluronic acid solutions or suspensions of collagen fragments. The drugs may be formulated in microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl)methylacrylamide]

and the like. Particular formations may be in the form of liquid suspensions, ointments, complexes to a bandage, collagen shield or the like. In some cases, for example where there is existing damage to the cornea, the compositions may be administered intradermally or possibly subcutaneously.

Administration into the eye is preferably via topical applications using eye drops, ointments, aerosols, or solid inserts. Eye drops and eye ointments are easily administered to the eye topically and have a rapid effect on target region. Another form of administration is microinjection into the eye of solubilized compounds. For example, microinjections can be made into a site near the trabecular meshwork or the Schlemm's canal. Microinjection is preferable to avoid side effects resulting from generalized exposure of the eye to a pharmaceutical compound. Microinjection may be used for infrequent administration, for example, weekly, biweekly, every few weeks, months, or even years, in contrast to the more frequent administrations required in the case of topical administration. Other forms of administration include tablets, capsules, powders, granules, etc. which may be administered orally and may have side effects or longer duration before efficacy.

Administration into the airways is preferably via inhalation or via physical application, using aerosols, solutions, and devices such as a bronchoscope. For inhalation, the compositions herein are conveniently delivered from an insufflator, a nebulizer, a pump, a pressurized pack, or other convenient means of delivering an aerosol, non-aerosol spray of a powder, or noon-aerosol spray of a liquid. Pressurized packs may comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide or other suitable gas is contemplated. In the case of a pressurized aerosol, the dosage unit may be determined by providing a valve to deliver a controlled amount. In administering a dry powder composition, the powder mix may include a suitable powder base such as lactose or starch. The powder composition may be presented in unit dosage form such as, for example, capsules, cartridges, or blister packs from which the powder may be administered with the aid of an inhalator or insufflator.

Administration to the vagina is preferably made via topical, vaginal applications, subcutaneous applications, or via microinjections into an affected area. The pharmaceutical compositions applied to the vagina may be in the form of a gel, cream, foam, ointment, aerosol, capsule, fluid, powder or suppository. Vaginal compositions may be administered directly to the target area (e.g., pelvic wall) or via an intravaginal device from which the composition is released. Administration to the vagina is preferably made in a time-release manner. The composition herein are preferably attached to a lipophilic or hydrophilic carrier and formulated in combination with a mucoadhesive agent to enhance adhesivity of the released compound to the vaginal mucosa and to assure contact with the vaginal mucosa. In order to enhance absorption of the compositions through the vaginal mucosa, an absorption enhancer or penetration promoter for intravaginally administered compounds is utilized as another formulating agent.

Administration to the rectum is preferably made via topical, rectal, and/or microinjections. Topical and rectal preparations are preferably formulated as suppositories with an oily excipient, such as cocoa butter. Microinjections are prepared as solutions and preferably formulated for slow release.

Amounts of pharmaceutical composition administered can vary, according to determinations made by one of skill, but preferably such amounts are effective to create an increase in the effective amount of L-arginine, increase in the effective amount of NO, and/or an increase in dilatory effect at the desired site without causing severe system hypotension. Furthermore, the amounts of composition administered may vary depending upon the individual, the condition being treated, the target site, additional agents in the composition or in treatment regimen, and the route by which the compositions are administered, all of which can be derived empirically according to methods known in the art.

In some embodiments, the compositions herein are co-administered with one or more additional therapeutic agents. Combination therapies according to this invention exert a synergistic effect of increasing NO in a cell, tissue and/or organ, or may act by an independent mechanism to treat the targeted condition. The use of such combinations is also advantageous to reduce the dosage of a given conventional therapeutic agent that would be required for a desired therapeutic or prophylactic effect as compared to when that agent is administered as a monotherapy. Combinations treatments may also reduce or eliminate the side effects of conventional single agent therapies. Combinations may also increase the efficacy of a conventional agent without increasing the associated toxicity. Preferred combination therapies include the administration of a compound of this invention with anti-inflammatories, antibiotics, diuretics, vasodilators, E2F Decoy, antiproliferatives, NO donors and NO releasing agents. When the compositions of this invention are administered in combination therapies with other agents, they may be administered sequentially or concurrently with such other agents to the patient.

As used herein a therapeutically effective amount is an amount, which upon a single or multiple doses produces a desired therapeutic effect by significantly increasing the levels of NO or L-arginine in a cell, tissue and/or organ. The dosages of NO enhancers used herein may vary depending upon the requirements of the patient in the judgment of the attending clinician, the severity of the condition being treated, and the particular compound being employed. In determining the therapeutically effective amount or dose of a NO enhancer (s), a number of factors should be considered by the attending clinician, including, but not limited to: the specific condition being treated, the pharmacodynamic characteristics of the particular compound being administered, the mode and route of administration, the desired time course of treatment, the species of mammal being treated, its size, age and general health, the degree of or involvement or severity of the disease, the response of the individual patient, the particular compound administered, the bioavailability characteristics of the preparation administered, the dose regimen selected, concurrent treatment (i.e., other co-administered therapeutic agents), and other relevant circumstances.

Generally, formulations of NO enhancers have a NO enhancer concentration of about 0.001 $\mu$M-100 mM, more preferably of about 0.01 $\mu$M-10 mM, more preferably of about 0.1 $\mu$M 1 mM, or more preferably of about 1 $\mu$M-500 $\mu$M. In some embodiments, formulations of NO enhancers are between 0.001 mg/ml-10 g/ml NO enhancer(s), more preferably 0.01 mg/ml-5 g/ml NO enhancer(s), more preferably 0.1 mg/ml-1 g/ml NO enhancer(s), or more preferably 1 mg/ml-500 mg/ml NO enhancer(s).

Of course, the concentration of NO enhancers may be higher or lower than any of the above dosages. The concentration of arginine polymers and/or homopolymers will depend, in part, on the percentage of L-arginine subunits and D-arginine subunits as well as other amino acid residues in the polymer.

The NO enhancers can be administered once or multiple times. Multiple administrations can be performed at intervals ranging from hourly, daily, weekly, biweekly, monthly, biyearly, yearly. However, intervals can also be more or less frequent than the above.

Upon improvement of a patient's condition, a maintenance dose of a composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment may cease or patients may require intermittent treatment on a long-term basis.

As the skilled artisan will appreciate, lower or higher doses than those recited above may be required. Specific dosage and treatment regimen for any particular patient will depend upon a variety of factors, including type, severity and course of the condition afflicting the patient; the activity of the specific composition employed, the age, sex, body, diet, weight, and general health status of the patient; the time, frequency, and route of administration; the patient's rate of excretion, and drug combination effects.

EXAMPLES

The following examples illustrate embodiments of the present invention.

Example 1

An AV graft is contacted with in a solution containing 0.001 µM-100 mm NO enhancer(s), e.g., R9 or R10. The graft is contacted with the solution for a period preferably less than 60 minutes. The graft is contacted prior to, during, and/or post grafting. In some cases, the graft is infused intraluminally with the L-arginine solution and one or both ends of the graft are clamped such that only the intraluminal walls of the vessel are contacted.

Example 2

An organ transplant solution (perfusate) preferably includes 0.001 µM-100 mM of a NO enhancer(s), e.g., R9 or R10. Furthermore, the solution may also include approximately 1-5% by weight hydroxyethyl starch. The solution can have a molecular weight ranging preferably between 150,000-350,000 Daltons. The solution can have an osmolality level ranging preferably between 100-500 mOsm/liter. Other agents that may be admixed into the solution include, but are not limited to, lactobionate salt, raffinose, electrolytes, glutathione, potassium phosphate, magnesium gluconate, adenosine, insulin, bactrim, dexamethasone, allopurinaol and other anti-inflammatory, antibiotic, anti-metabolic, and anti-neoplastic agents

Example 3

For the treatment of peripheral arterial disease, a drug eluting stent may be coated or immersed with a timed-release NO enhancer, e.g. an arginine homopolymer containing L-arginines, D-arginines, or a combination thereof. An additional slow release carrier or excipient may be admixed with the polyarginine. Alternatively, a stent or balloon can be inserted into the targeted area (an occlusion), and a Dispatch catheter can deliver locally and in vivo a composition of R9 (SEQ. ID NO. 2) (e.g., a solution of 0.001 .mu.-100 mM R9 (SEQ. ID NO. 2)) prior to, during, and/or post stenting or angioplasty.

Example 4

A graft used for CABG may be immersed ex vivo in a solution comprising of 0.001µ-100 mM of a NO enhancer, e.g., R9, for 10-20 minutes at room temperature. The solution can be either serum free culture media (e.g., DMEM) or aqueous saline NaCl solution (e.g., 0.5-2.0% (w/v) saline. Alternatively, a graft may be immersed ex vivo in any of the transplant or perfusate solutions disclosed herein. Furthermore, a graft can be contacted with any of the above solutions in vivo either prior its excision from a body or post transplantation.

Example 5

A female diagnosed with vulvodynia is treated with one or more microinjections of a solution comprising a NO enhancer, e.g., R9 (SEQ. ID NO. 2) or R10 (SEQ. ID NO. 3). The solution comprises 0.001 .mu.M-100 mM R9 (SEQ. ID NO. 2) or R10 (SEQ. ID NO. 3). Alternatively, a composition of R9 or R10 is formulated into a solid suppository or a gel and administered vaginally at dosages ranging between 0.001 mg to 10 g per application or day. The formulations may be admixed with additional therapeutic agents such as muscle-relaxers or painkillers.

Example 6

A patient diagnosed with glaucoma is treated with a NO enhancer composition comprising, e.g., R9 or R10. The composition can be administered topically or subcutaneously (e.g., via microinjections) to the outer aspect of the trabecular meshwork or inner walls of the Schlemm's canal. The composition can be formulated as a solution, ointment or gel. The composition can further include any one or more of the following agents: pilocarpine, timolol maleate, betataxolol HCl, epinephrine, dipivefrin, demecarium bromide, echothiophate iodide, carbonic anydrase inhibitors, alkaloids, atrial natriuretic factor peptides, substituted 2-aminotetralins, phenylimino-imidazoles, betaxolol salts, minoxidil, nitroglycerin, isosorbide dinitrate, nitroprusside, cyclic guanosine 3',5'-monophosphate specific phosphodiesterase type 5 (cGMP-PDE5) inhibitor, A3 subtype adenosine receptor antagonists, calmodulin antagonists, antiestrogens, potassium channel blockers, oncomodulin, a cAMP modulator, and 15-keto-prostaglandin.

Example 7

A patient diagnosed with anal fissures may be treated with a NO enhancer composition comprising, e.g., R9 or R10. The composition can be administered topically or subcutaneously. The composition can further include anesthetics, painkillers, antibacterial, antifungal, and anti-inflammatories. The composition can be formulated into a gel, cream or a solution and administered rectally to the patient at dosages of 0.001 mg to 10 g per day.

Example 8

A patient diagnosed with pulmonary arterial hypertension may be treated with a NO enhancer composition comprising, e.g., R9 (SEQ. ID NO. 2) or R10 (SEQ. ID NO. 3). The composition can be administered by inhalation. The NO enhancer is formulated as an aerosol solution and may further comprise an anesthetic, painkiller, antibacterial, antifungal, anti-inflammatory, and calcium channel blockers. The solution preferably includes 0.001 .mu.M-100 mM of the NO enhancer and is administered at regular intervals, e.g., hourly, daily, weekly, or as needed.

Example 9

A patient diagnosed with erectile dysfunction is treated with local administration of a NO enhancer(s). The NO enhancer(s), e.g., R9 (SEQ. ID NO. 2) or R10 (SEQ. ID NO. 3), can be administered, for example, subcutaneously by microinjection or topically by applying a gel or a solution directly to the penis, the penile arterial blood vessel, and/or the trabecular meshwork. The solution or composition to be administered comprises 0.001 .mu.M-100 mM or may be applied in dosages ranging from 0.001 mg to 10 g per application. The compositions can also include additional therapeutic agents.

The above examples and description are provided only for the purpose of illustrations and are not intended to limit the invention in any way. As will be appreciated by the skilled person, the invention can be carried out in a great variety of ways, employing more than one technique from those described above, all without exceeding the scope of the invention. All of the references and publications disclosed herein are incorporated by references in their entirety for all purposes.

What is claimed is:

1. A method for treating vulvodynia in a patient comprising administering locally to said patient a therapeutically effective amount of an arginine polymer comprising at least 8 consecutive arginine residues.

2. The method of claim 1 wherein said composition is an arginine homopolymer.

3. The method of claim 2 wherein said arginine homopolymer consists essentially of L-arginine residues.

4. The method of claim 1 wherein said composition is administered subcutaneously, topically, or vaginally.

5. The method of claim 3 wherein said composition is administered topically.

\* \* \* \* \*